United States Patent [19]
Peters, Jr. et al.

[11] 3,947,337
[45] Mar. 30, 1976

[54] α,ω-DIARYLPOLYENE PHOTOSENSITIZERS FOR SULFONYLAZIDE POLYMERS

[75] Inventors: Gerret M. Peters, Jr., Meriden; Fred A. Stuber, North Haven; Henri Ulrich, Northford, all of Conn.

[73] Assignee: The Upjohn Company, Kalamazoo, Mich.

[22] Filed: Dec. 23, 1974

[21] Appl. No.: 535,706

Related U.S. Application Data

[63] Continuation-in-part of Ser. No. 359,132, May 10, 1973, Pat. No. 3,879,463.

[52] U.S. Cl............ 204/159.15; 96/91 N; 96/115 R; 204/159.18; 260/47 VA; 260/49; 260/78.5 T; 260/79.5 NV; 260/875; 260/879; 260/886

[51] Int. Cl.².. C08F 8/00; C08F 8/34; C08L 25/04; G03C 1/68

[58] Field of Search.................. 204/159.15, 159.18; 260/78.5 T, 79.5 NV; 96/115 R, 91 N

[56] References Cited
UNITED STATES PATENTS

| | | | |
|---|---|---|---|
| 2,852,556 | 9/1958 | Katz et al. | 260/578 |
| 3,714,194 | 1/1973 | Ulrich et al. | 96/91 N |
| 3,721,566 | 3/1973 | Laridon et al. | 96/91 N |
| 3,770,846 | 11/1973 | Stuber et al. | 204/159.14 |
| 3,804,628 | 4/1974 | Osada et al. | 204/159.18 |
| 3,843,603 | 10/1974 | Gates | 96/91 N |
| 3,865,597 | 2/1975 | Broyde | 204/159.18 |

*Primary Examiner*—Murray Tilman
*Assistant Examiner*—Thurman K. Page
*Attorney, Agent, or Firm*—Denis A. Firth; John Kekich

[57] ABSTRACT

A novel class of compounds is disclosed of the formula

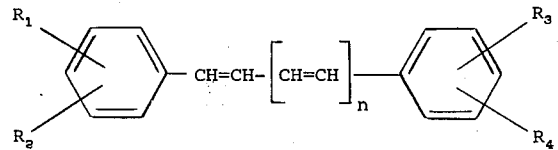

wherein $R_1$ and $R_2$ are lower-alkoxy or di(lower-alkyl)amino and $R_1$ can be hydrogen and $R_3$ and $R_4$ are hydrogen, lower-alkoxy or di(lower-alkyl)amino and $n$ is an integer from 1 to 5. The compounds are sensitizers for photosensitive compounds particularly polymers containing sulfonazido groups as the light-sensitive moiety.

5 Claims, No Drawings

α,ω-DIARYLPOLYENE PHOTOSENSITIZERS FOR SULFONYLAZIDE POLYMERS

CROSS-REFERENCE TO RELATED APPLICATIONS

This application is a continuation-in-part of application Ser. No. 359,132 filed May 10, 1973, and now U.S. Pat. No. 3,879,463.

BACKGROUND OF THE INVENTION

1. Field of the Invention

This invention relates to novel polymers and is more particularly concerned with α,ω-diaryl polyenes and with methods for their preparation and methods for their use as photosensitizers.

2. Description of the Prior Art

To the best of our knowledge the compounds of the invention are novel. Nuclear unsubstituted α,ω-diaryl polyenes e.g. 1,4-diphenyl butadiene, are well-known in the art but show no ability to act as photosensitizers when used in the context described hereinafter.

SUMMARY OF THE INVENTION

The invention comprises compounds of the formula:

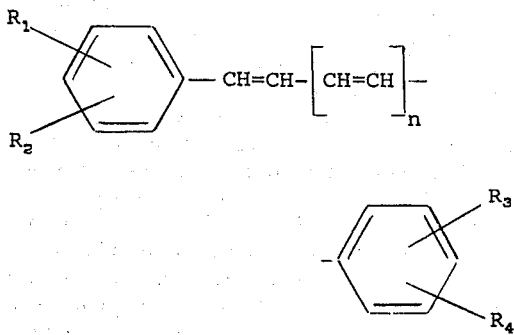

(I)

wherein $R_1$ is selected from the group consisting of hydrogen, lower-alkoxy and di(lower-alkyl)amino, $R_2$ is selected from the group consisting of lower-alkoxy and di(lower-alkyl)amino, and $R_3$ and $R_4$ are independently selected from the group consisting of hydrogen, loweralkoxy and di(lower alkyl)amino, and $n$ is an integer from 1 to 5.

The term "lower-alkyl" means alkyl from 1 to 6 carbon atoms, inclusive, such as methyl, ethyl, propyl, butyl, pentyl, hexyl, and isomeric forms thereof. The term "lower-alkoxy" means alkoxy from 1 to 6 carbon atoms, inclusive, such as methoxy, ethoxy, propoxy, butoxy, pentyloxy, hexyloxy and isomeric forms thereof.

The compounds of the invention are useful as photosensitizers and are more particularly useful in sensitizing light-sensitive polymers containing sulfonylazide groups to radiation of wavelengths to which said polymers are not normally sensitive. These uses will be discussed in more detail hereinafter.

DETAILED DESCRIPTION OF THE INVENTION

The novel compounds of the formula (I) are conveniently prepared by the method which is illustrated schematically as follows:

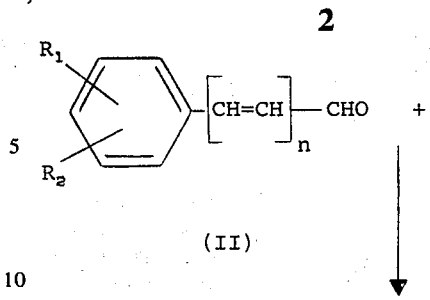

(II)

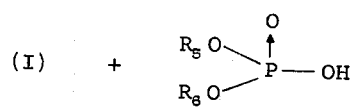

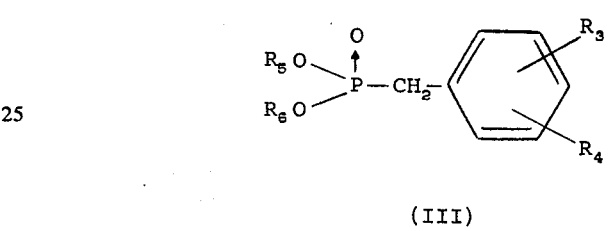

(III)

wherein n, $R_1$, $R_2$, $R_3$, and $R_4$ are as hereinbefore defined, and $R_5$ and $R_6$ represent lower-alkyl.

The reaction of the unsaturated aldehyde (II) and the benzylphosphonate (III) is carried out advantageously by bringing the reactants together in the presence of a strong base and an inert organic solvent. Examples of strong bases are sodium hydride, potassium hydride, lithium hydride, sodamide, sodium ethoxide, potassium tert-butoxide and the like. The term inert organic solvent means an organic solvent which is inert under the conditions of the reaction i.e. does not enter into or interfere with the desired course of the reaction. Examples of inert organic solvents are dimethoxyethane, benzene, toluene, xylene, hexane, heptane, tetrahydrofuran, dimethylformamide, and the like.

The reactants (II) and (III) are employed in approximately stoichiometric proportions. The reaction is preferably carried out at elevated temperature within the range of about 60°C to about 85°C. The course of the reaction is followed by routine procedures e.g. by spectroscopic analysis of aliquots, and when the reaction is judged to be complete the desired polyene (I) is isolated therefrom by procedures well-known in the art. For example, the solvent can be removed by distillation and the residue purified by recrystallization, chromatography, fractional precipitation and like techniques.

The unsaturated aldehydes (II) and the benzylphosphonates (III) which are employed as starting materials in the preparation of the compounds of the invention are for the most part known in the art and are prepared by known techniques. For example the unsaturated aldehydes (II) can be prepared by condensation of the corresponding substituted benzaldehydes

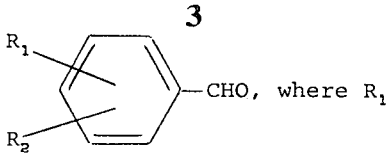

where $R_1$ and $R_2$ have the significance hereinbefore defined, with acetaldehyde in the presence of sulfuric acid in accordance with the conditions described by König et al., Berichte, 61, 2074, 1928 or Jutz, Berichte, 91, 850, 1958. An alternative, and elegant, method of preparing the compounds (II) from the corresponding substituted benzaldehyde is described by Marshall et al. J. Chem. Soc. 1956, 4082.

The benzylphosphonates (III) are readily prepared by refluxing a mixture of the appropriate tri(loweralkyl)phosphite and the appropriate benzyl chloride

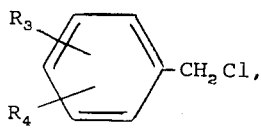

wherein $R_3$ and $R_4$ are as hereinbefore
defined, with elimination of lower-alkyl chloride, in accordance with procedures well-known in the art for the preparation of phosphonates.

The compounds of the invention of the formula (I) find particular use as sensitizers for light-sensitive material. In particular, it has been found that the compounds of formula (I) can be used to sensitize light-sensitive polymers containing sulfonylazide groups to radiation of wavelengths which do not normally activate such polymers. For example, the sulfonylazido-containing light sensitive polymers which are described in copending application Ser. No. 93,446, filed Nov. 27, 1970, now U.S. Pat. No. 3,784,527 in the names of Adnan A. R. Sayigh, Fred A. Stuber and Henri Ulrich, are derived by reacting copolymers of maleic anhydride and styrene, or copolymers of maleic anhydride and methyl vinyl ether, with a hydroxyalkyl azidosulfonyl carbanilate. This results in opening of the anhydride moieties of the starting copolymer to give recurring units having a free carboxy group and an esterified carboxy group containing a sulfonylazide group in the ester moiety. These light sensitive polymers are useful, amongst other things, in the preparation of continuous tone images, in rendering hydrophilic the surface of substrates to which said polymers can be bonded by exposure to suitable radiation, and in the preparation of photoresists.

However, said light sensitive polymers, when used without sensitizers, are activated by light of wavelength about 260 to 330 nm, i.e. in the ultraviolet spectrum. This means that special, and relatively expensive, sources of radiation need to be used in conjunction with these polymers. In has accordingly become desirable to sensitize said polymers in such a manner that they can be activated by radiation in the wavelengths of the order of 400–500 nm so that much cheaper and more readily accessible sources of radiation e.g. tungsten lamps, could be used.

The use of the compounds of formula (I) has made it possible to sensitize said light-sensitive polymers in the desired manner so as to render them activatable by radiation in the range of 400–500 nm. In using the compounds of the formula (I) as sensitizers it is merely necessary to incorporate them into the composition in which the light-sensitive polymer is applied to the substrate. In general the light-sensitive polymer is applied to the substrate in the form of a film by use of a solution of the light-sensitive polymer in a suitable solvent such as acetone, acetonitrile, methyl ethyl ketone and the like. In this case the sensitizer of formula (I) is incorporated into a solution of the light-sensitive polymer before said solution is applied to the substrate. Advantageously the sensitizer of formula (I) is employed in a proportion of about 10 parts to about 20 parts by weight per 100 parts of light-sensitive polymer.

The above findings are all the more surprising in view of the fact that the closely related compound, 1,4-diphenyl-1,3-butadiene shows no sensitizing properties when employed under identical conditions to those described above.

The following preparation and examples describe the manner and process of making and using the invention and set forth the best mode contemplated by the inventors of carrying out the invention but are not to be construed as limiting.

Preparation 1. 0,0-diethyl 2,5-dimethoxybenzylphosphate

A mixture of 3.5 g (18.8 mmole) of 2,5-dimethoxybenzyl chloride (Kost et al., Zh. Obshch. Khim, 33, 2011, 1963; Chemical Abstracts 62, 16089h, 1965) and 25 g. (150 mmole) of triethylphosphite (previously dried over metallic sodium) was heated under reflux for 24 hours. The resulting mixture was subjected to fractional distillation under reduced pressure. After removal of excess triethylphosphite the fraction which distilled at 145° to 147°C at a pressure of less than 1 mm. of mercury was collected. There was thus obtained 0,0-diethyl 2,5-dimethoxybenzylphosphonate in the form of a colorless liquid which exhibited a bluish fluorescence when exposed to ultraviolet light. The nmr spectrum was in agreement with the assigned structure.

Similarly, using the above procedure, but replacing 2,5-dimethoxybenzyl choride by 4-dimethylaminobenzyl chloride, 3-methoxy-4-dimethylaminobenzyl chloride, or 3-methoxybenzyl chloride, there were obtained 0,0-diethyl 4-dimethylaminobenzylphosphonate, 0,0-diethyl 3-methoxy-4-dimethylaminobenzylphosphonate and 0,0-diethyl 3-methoxybenzylphosphonate, respectively.

Preparation 2.

Using the procedure described by Konig et al., supra, for the preparation of 4-dimethylaminocinnamaldehyde but replacing the 4-dimethylaminobenzaldehyde employed as starting material by 2,5-dimethoxybenzaldehyde, there was obtained 2,5-dimethoxycinnamaldehyde.

EXAMPLE 1.

1-(2,5-dimethoxyphenyl)-4-(4-dimethylaminophenyl)-butadiene.

To a mixture of 5 g. (28.5 mmoles) of 4-dimethylaminocinnamaldehyde (Konig et al, supra) and 8.2 g. (28.5 mmole) of 0,0-diethyl 2,5-dimethoxybenzylphosphonate (Preparation 1) in approximately 30 ml. of 1,2-dimethoxyethane was added 0.7 g. (29 mmoles) of sodium hydride. The resulting mixture was heated under reflux for 90 minutes. The mixture was cooled to room temperature, the supernatant liquor was decanted from the orange gummy material which had settled out and the latter was washed with circa 50 ml. of 1,2-dimethoxyethane. The washings and the supernatant were combined and concentrated to about 60 ml. by evaporation before being poured into circa 300 ml. of water. The solid material which separated was isolated by filtration and recrystallized from ethanol. There was thus obtained 2.7 g. of 1-(2,5-dimethoxyphenyl)-4-(4-dimethylaminophenyl)-butadiene in the form of a crystalline solid having a melting point of 118° to 120°C. The UV spectrum of this material (2 × $10^{-5}$ molar solution in acetonitrile) exhibited a maximum at 380 nm ($\epsilon$ = 49,500). The nuclear magnetic resonance spectrum was also in accordance with the assigned structure.

In order to assess the efficiency of the above compound in extending the sensitivity of a sulfonylazide photosensitive polymer to radiation of wavelength of the order of 400 nm. the following experiments were carried out.

A solution of 2.2 parts by weight of Photozid (a light-sensitive sulfonylazide polymer obtained by reacting a maleic anhydride - vinyl methyl ether copolymer with 2-hydroxyethyl 4-azidosulfonylcarbanilate; The Upjohn Company) and 0.22 parts by weight of the above butadiene in 100 parts of methyl ethyl ketone was used to whirler cast films of light-sensitive polymer on strips of Mylar. Individual coated Mylar strips were then exposed, via a negative image comprising a pattern of dots, to radiation of wavelengths 400 nm., 404 nm. and 435 nm. (produced by use of appropriate filters which excluded all other frequencies from the radiation produced by an Osram XBO 150 watt high pressure Xenon lamp.) The exposure times were 30 seconds for 400 nm. wavelength, 3 minutes for the 404 nm. and 10 minutes for the 435 nm. radiation. After exposure the irradiated Mylar strips were developed by immersion for 60 seconds in a bath containing a mixture of 5 parts of methyl ethyl ketone and 1 part of 4-methyl-2-pentanone. The developed strips were the dyed by immersion for 60 seconds in a 1 percent w/w aqueous solution of Basic Blue 9. A clear blue image was achieved on all test strips. In contrast, strips which were prepared and irradiated in exactly the same manner but either omitting the butadiene from the initial polymer solution or replacing said butadiene by an equal weight of 1,4-diphenyl butadiene, showed no image thus indicating that, in the absence of the above butadiene sensitizer or when said butadiene was replaced by 1,4-diphenylbutadiene, the Photozid had not been activated by the radiation of the above wavelengths.

EXAMPLE 2.

Using the procedure described in Example 1, but replacing 4-dimethylaminocinnamaldehyde by 1-(4-dimethylaminophenyl)-1,3-pentadien-5-al (Jutz, supra) there was obtained 1-(2,5-dimethoxyphenyl)-6-(4-dimethylaminophenyl)-1,3,5-hexatriene.

Similarly, using the procedure described in Example 1, but replacing 4-dimethylaminocinnamaldehyde by 1-(4-dimethylaminophenyl)-1,3,5-heptatrien-7-al, there was obtained 1-(2,5-dimethoxyphenyl)-8-(4-dimethylaminophenyl)-1,3,5,7-octatetraene.

EXAMPLE 3.

Using the procedure described in Example 1, but replacing 0,0-diethyl 2,5-dimethoxybenzylphosphonate by 0,0-diethyl 3-methoxy-4-dimethylaminobenzylphosphonate or 0,0-diethyl 3-methoxybenzylphosphonate, there were obtained:
1-(3-methoxy-4-dimethylaminophenyl)-4-(4-dimethylaminophenyl)butadiene, and 1-(3-methoxyphenyl)-4-(4-dimethylaminophenyl) butadiene, respectively.

EXAMPLE 4.

Using the procedure described in Example 1, but replacing the 4-dimethylaminocinnamaldehyde there used by 2,5-dimethoxycinnamaldehyde, there was obtained 1,4-di(2,5-dimethoxyphenyl)butadiene.

Similarly, using the procedure described in Example 1, but replacing 4-dimethylaminocinnamaldehyde by
4-ethoxy-3-methoxycinnamaldehyde (J. Amer. Chem. Soc. 72, 2501, 1950)
4-methoxycinnamaldehyde (J. Chem. Soc. 1956, 4082)
1-(4-methoxyphenyl)-1,3-pentadien-5-al (ibid)
1-(4-methoxyphenyl)-1,3,5-heptatrien-7-al (ibid) or
1-(4-methoxyphenyl)-1,3,5,7-nonatetraen-9-al, there were obtained:
1-(2,5-dimethoxyphenyl)-4-(4-ethoxy-3-methoxyphenyl) butadiene,
1-(2,5-dimethoxyphenyl)-4-(4-methoxyphenyl)-butadiene,
1-(2,5-dimethoxyphenyl)-6-(4-methoxyphenyl)-1,3,5-hexatriene,
1-(2,5-dimethoxyphenyl)-8-(4-methoxyphenyl)-1,3,5,7-octatetraene, and
1-(2,5-dimethoxyphenyl)-10-(4-methoxyphenyl)-1,3,5,7,9-decapentaene, respectively.

EXAMPLE 5.

1,4-di(4-dimethylaminophenyl)-1,3-butadiene

To a mixture of 5 g. (18.4 mmoles) of 0,0-diethyl 4-dimethylaminobenzylphosphonate (Preparation 1) and 3.2 g. (18.4 mmoles) of 4-dimethylaminocinnamaldehyde in 40 ml. of 1,2-dimethoxyethane was added 0.6 g. (25 mmole) of sodium hydride. The resulting mixture was heated under reflux for 2.25 hours. At the end of this period the mixture was cooled and poured into 300 ml. of cold water. The orange-tan solid which separated was extracted with chloroform and the chloroform extract was dried over anhydrous sodium sulfate. The dried extract was evaporated to dryness and the residue was recrystallized from ethanol. There was thus obtained 1,4-di(4-dimethylaminophenyl)-1,3-butadiene in the form of an orange yellow solid having a melting point of 234° to 240°C. The ultraviolet spectrum of this material (acetonitrile) exhibited a maximum at 385 nm ($\epsilon_{385}$ = 72,200). The nuclear magnetic resonance spectrum was also in accordance with the assigned structure.

The above compound was then used to sensitize Photozid according to the procedure described at the end of Example 1, supra. It was found that a clear blue image was obtained using radiation of wavelength 435 nm.

EXAMPLE 6.

1-(2,5-dimethoxyphenyl)-4-phenyl-1,3-butadiene

To a mixture of 10 g. (76 mmole) of cinnamaldehyde and 22 g. (76 mmole) of 0,0-diethyl 2,5-dimethoxybenzylphosphonate (Preparation 1) in 60 ml. of freshly distilled 1,2-dimethoxyethane was added 2 g. (76 mmole) of sodium hydride. The resulting mixture was heated under reflux for 3 hours. At the end of this time the reaction mixture was cooled and filtered to remove a yellow solid. The filtrate was diluted with water and extracted with chloroform. The chloroform extract was dried over anhydrous magnesium sulfate and the dried extract was evaporated to dryness. There was thus obtained 16 g. of 1-(2,5-dimethoxyphenyl)-4-phenyl-1,3-butadiene in the form of an orange yellow viscous liquid. A sample (4.1 g.) of this material was purified by dissolving in benzene and subjecting to chromatography on a column of silica gel using benzene as the eluent. The ultraviolet absorption spectrum (acetonitrile solution) of the purified material exhibited maxima at 315 nm. ($\epsilon = 27,586$) and 355 nm. ($\epsilon = 26,875$). The nuclear magnetic resonance spectrum of the purified material was in accord with the assigned structure.

We claim:

1. A process for sensitizing a light-sensitive polymer containing sulfonazide groups to radiation of a wavelength greater than 400 nm said polymer being the product of reaction of a hydroxyalkyl azidosulfonyl carbanilate with a polymer selected from the class consisting of copolymers of maleic anhydride and styrene and copolymers of maleic anhydride and methyl vinyl ether which process comprises exposing said light-sensitive polymer to said radiation in the presence of a sensitizing amount of a compound having the formula:

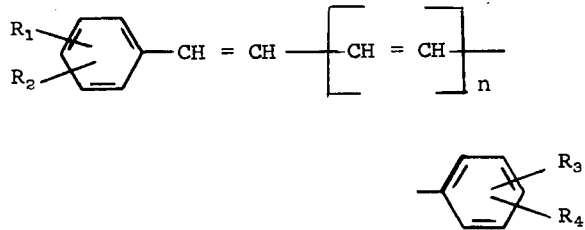

wherein $R_1$ is selected from the group consisting of hydrogen, lower-alkoxy and di(lower-alkyl)amino, $R_2$ is selected from the group consisting of lower-alkoxy and di(lower-alkyl)amino, and $R_3$ and $R_4$ are independently selected from the group consisting of hydrogen, lower-alkoxy and di(lower-alkyl)amino and n is an integer from 1 to 5.

2. A process according to claim 1 wherein the sensitizing compound is 1,4-di(4-dimethylaminophenyl)-1,3-butadiene.

3. A process according to claim 1 wherein the sensitizing compound has the formula:

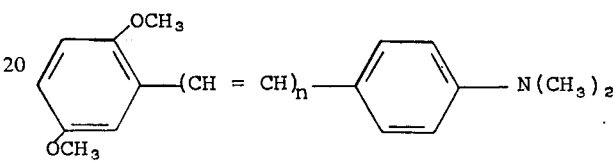

wherein $n$ is an integer from 2 to 4.

4. A process according to claim 1 wherein the sensitizing compound is 1-(2,5-dimethoxyphenyl)-4-(4-dimethylaminophenyl)-1,3-butadiene.

5. A process according to claim 1 wherein the sensitizing compound is 1-(2,5-dimethoxyphenyl)-6-(4-dimethylaminophenyl)-1,3,5-hexatriene.

* * * * *